(12) United States Patent
Dreyer

(10) Patent No.: US 8,101,635 B2
(45) Date of Patent: *Jan. 24, 2012

(54) CALCIUM BLOCKERS TO TREAT PROLIFERATIVE VITREORETINOPATHY

(75) Inventor: Evan B. Dreyer, Pittsburgh, PA (US)

(73) Assignee: Allergan, Inc., Irvine, CA (US)

( * ) Notice: Subject to any disclaimer, the term of this patent is extended or adjusted under 35 U.S.C. 154(b) by 1392 days.

This patent is subject to a terminal disclaimer.

(21) Appl. No.: 10/885,422

(22) Filed: Jul. 6, 2004

(65) Prior Publication Data

US 2005/0192322 A1 Sep. 1, 2005

Related U.S. Application Data

(63) Continuation of application No. 10/436,902, filed on May 12, 2003, now Pat. No. 7,230,032, which is a continuation of application No. 10/038,215, filed on Jan. 2, 2002, now Pat. No. 6,573,280, which is a continuation of application No. 09/445,832, filed as application No. PCT/US98/12414 on Jun. 15, 1998, now Pat. No. 6,380,261.

(60) Provisional application No. 60/051,962, filed on Jun. 30, 1997.

(51) Int. Cl.
*A61K 31/445* (2006.01)
*A61K 31/135* (2006.01)
(52) U.S. Cl. .......................... 514/317; 514/646; 514/912
(58) Field of Classification Search .................. 514/317, 514/646, 912
See application file for complete search history.

(56) References Cited

U.S. PATENT DOCUMENTS

| | | | |
|---|---|---|---|
| 4,690,931 A | 9/1987 | Wick et al. | |
| 4,755,388 A | 7/1988 | Papahadjopoulos et al. | |
| 5,424,321 A | 6/1995 | Hellberg et al. | |
| 5,431,907 A | 7/1995 | Abelson et al. | |
| 5,516,522 A | 5/1996 | Peyman et al. | |
| 5,521,215 A | 5/1996 | Mechoulam et al. | |
| 5,527,810 A | 6/1996 | Ornstein | |
| 5,547,963 A | 8/1996 | Poindron et al. | |
| 5,597,809 A | 1/1997 | Dreyer | |
| 5,602,156 A | 2/1997 | Kohn | |
| 5,604,244 A | 2/1997 | DeSantis, Jr. et al. | |
| 5,623,051 A | 4/1997 | Catterall et al. | |
| 5,710,165 A | 1/1998 | Kapin et al. | |
| 5,922,773 A | 7/1999 | Lipton et al. | |
| 6,482,854 B1 | 11/2002 | Lipton et al. | |

FOREIGN PATENT DOCUMENTS

| | | |
|---|---|---|
| FR | 2738568 | 3/1997 |
| WO | WO 90/06118 | 6/1990 |
| WO | WO 91/02497 | 3/1991 |
| WO | WO 94/13275 | 6/1994 |
| WO | WO 95/22979 | 8/1995 |
| WO | WO 97/09309 | 3/1997 |
| WO | WO 97/09310 | 3/1997 |

OTHER PUBLICATIONS

Constable I: "Biological and Therapeutic Aspects of Proliferative Vitreoretinopathy" Japanese Journal of Ophthalmology, vol. 31, No. 4, 1987, pp. 513-520, XP008054876.
Uchida N. et al: "Glutamate Stimulates Proliferation of Retinal Pigment Epithelium and Its BFGF Expression Through NMDA Receptor Activation", vol. 71, No. Suppl. 1, Mar. 20, 1996, p. 274P, XP008040806.
Murphy T L et al: "Migration of retinal pigment epithelium cells in vitro is regulated by protein kinase C", Experimental Eye Research, vol. 60, No. 6, Jun. 1995, pp. 683-695, XP-002102540.
Uchida N. et al: "Gltamate-Stimulated Proliferation of Rat Retinal Pigment Epithelium: Through NMDA Receptor Activation and BFGF Expression", Investigative Ophthalmology & Visual Science, vol. 37, No. 3, Apr. 21, 1996, pp. S388, XP008040803.
Sakamoto T et al: "Vitamin E Succinate Inhibits Proliferation and Migration of Retinal Pigment Epithelial Cells in Vitro-Therapeutic Implication for Proliferative Vitreoretinopathy", Graefe's Archive for Clinical and Experimental Ophthalmology, vol. 234, No. 3, Mar. 1996, XP008040829.
Hackett S. et al: Cyclic 3',5'-Adenosine Monophosphate Modulates Retinal Pigment Epithelial Cell Migration in Vitro, vol. 104, No. 11, Nov. 1986, pp. 1688-1692, XP008054877.
Hackett S. et al: "Implication of Protein Carboxymethylation in Retinal Pigment Epithelial Cell Chemotaxis", Ophthalmic Research, vol. 20, No. 1, 1988, pp. 54-59.
Wagner M. et al: "Effects of Pharmacological Modulation of Intracellular Signalling Systems on Retinal Pigment Epithelial Cell Attachment to Extracellular Matrix Protein", Current Eye Research, vol. 14, No. 5, May 1995, pp. 373-384.
Kalloniatis M.:"Amino Acids in Neurotransmission and Disease", Journal of the American Optometric Assoc., vol. 66, No. 12, Dec. 1995, pp. 750-757, XP008053708.
Solberg Y et al: "Treatment of Laser-Induced Retinal Injuries by Neuroprotection", SPIE, vol. 2974, 1997, pp. 158-165.
Ishikawa S. et al: "Alteration of Glutamine Concentration in the Vitreous Humor in Patients with Proliferative Vitreoretinopathy", Current Eye Research, vol. 14, No. 3, Mar. 1995, pp. 191-197, XP008053697.
Haberecht M. et al: "N-Methyl-D-Aspartate-Mediated Glutamate Toxicity in the Developing Rabbit Retina" Journal of Neuroscience Research, vol. 47, No. 4, Feb. 15, 1997, pp. 416-426, XP008040828.
Uchida et al: "Glutamate-Stimulated Proliferation of Rat Retinal Pigment Epithelial Cells", European Journal of Pharmacology, vol. 343, No. 2/3, Feb. 19, 1998, pp. 265-273, XP008040812.
Machamer (1978) British J. Ophthal. 62:737.
Hilton et al (1983) Ophthalmology 90:121.

(Continued)

*Primary Examiner* — Zohreh Fay
(74) *Attorney, Agent, or Firm* — John E. Wurst; Kevin J. Forrestal; Doina G. Ene

(57) ABSTRACT

Glutamate causes migration and proliferation of retinal pigment epithelium and/or glial cells, and glutamate antagonists can prevent, treat or reduce retinal pigment epithelium and/or glial migration and the subsequent development of proliferative vitreoretinopathy. Avoidance or management of proliferative vitreoretinopathy can be achieved by administering to the patient a compound capable of reducing glutamate-induced retinal cell migration in a concentration effective to reduce such migration.

18 Claims, No Drawings

OTHER PUBLICATIONS

Sommer et al, "Glutamate receptor channels: novel properties and new clones", Trends Pharmacological Sciences 13:291-296 (1992).
Nakanishi, "Molecular Diversity of glutamate receptors and implications for brain function", Science 248: 597-603 (1992).
Karschian et al, J. Physiol. 418: 379-396 (1989).
Watkins et al, Trends in Pharmacological Sci 11:25 (1990).
Bean, Annual Rev. Neurosci. 51:367-384 (1989).
Hess, Annual Rev. Neurosci. 13:337-356 (1990).
Kiumura et al, Human Gene Therapy, 7:799-808 (1996).
Sakamoto et al, Ophthalmology 102: 1417-1421 (1995).
Handa et al, Experimental Eye Research 62: 689-696 (1996).
Berger et al 37: 2318-2325 (1996).
de Souza et al, Ophthalmologica 209: 212-216 (1995).
Nakagawa et al, Ophthalmology & Visual Science 36: 2388-2395 (1995).
Steinhorst et al, Archive for Clinical & Experimental Ophthalmology 232: 347-354 (1994).
Young, Richard W., "Solar radiation and age-related macular degeneration," *Sur. Ophthal.*, vol. 32(4):252-269, Jan.-Feb. 1988.
Bressler, et al., "Age-related macular degeneration," *Sur Ophthal.*, vol. 32(6):375-413, May-Jun. 1988.
Curcio, et al., "Photoreceptor loss in age-related macular degeneration," *Invest. Ophthal. & Vis. Sci*, vol. 37(7):1236-1249, Jun. 1996.
Ge-Zhi, et al., "Apoptosis in human retinal degenerations," *Trans AM Ophthal. Soc.*, vol. 94, 411-431, 1996.
Marshall, et al., "Histopathology of ruby and argon laser lesions in monkey and human retina," *British Journal of Ophthalmology*, vol. 59:610-613, 1975.
Taylor, et al., "Long-term effects of visible light on the eye," *Arch. Ophthal.*, vol. 110:99-104, Jan. 1992.
Naash, et al., "Light-induced acceleration of photoreceptor degeneration in transgenic mice expressing mutant rhodopsin," *Invest. Ophthal. & Vis. Sci.*, 1996, vol. 37(5):775-782, Apr. 1996.
Cruickshanks, et al., "Sunlight and age-related macular degeneration. The Bever Dam eye study," *Archives of Ophthalmology*, vol. 111:514-518, 1993.
Faktorovich, et al., "Photoreceptor degeneration in inherited retinal dystrophy delayed by basic fibroblast . . . ," *Nature*, vol. 347:83-86, Sep. 6, 1990.
Li, et al., "Amelioration of photo injury in rat retina by ascorbic acid: A histopthologic study," *Invest. Ophthal. & Vis. Sci.*, vol. 26:1589-1598, Nov. 1985.
Organisciak, et al., "Protection by dimethylthiourea against retinal light damage in rats." *Invest. Ophthal. & Vis. Sci.*, vol. 33(5):1599-1609, Apr. 1992.
Lam, et al., "Amelioration of retinal photoic injury in albino rats by dimethylthiourea," *Arch Ophthal.*, vol. 108, 1751-1757, 1990.
Kozaki, et al., Light-induced retinal damage in pigmented rabbit-2. Effect of alpha-tocopherol, *Nippon Ganka Gakkai Zasshi*, vol. 98(10):948-954, Oct. 1994.
Rapp, et al., "Evaluation of retinal susceptibility to light damage in pigmented rats supplemented with beta-Carotene," *Cur. Eye Res.* vol. 15, 219-223, 1995.
Li, et al., "Amelioration of retinal photic injury by a combination of flunarizine and dimethylthiourea," *Exp. Eye Res.*, vol. 56:71-78, 1993.
Edward, et al., "Amelioration of light-induced retinal degeneration by a calcium overload blocker," *Arch Ophthal.*, vol. 109:554-562, Apr. 1991.
LaVail, et al., "Multiple growth factors, cytokines, and neurotrophins rescue photoreceptors from the damaging effects of constant light," *Proc. Nat. Acad. Sci.*, vol. 89:11249-11253, Dec. 1992.
Lam, et al., "Methylprednisolone therapy in laser injury of the retina," *Graefes Arch. Clin. Exp. Ophthal.*, vol. 231:729-736, 1993.
Fu, et al., "Dexamethasone ameliorates retinal photic injury in albino rats," *Exp. Eye Res.* vol. 54:583-594, 1992.
Li, et al., "Desferrioxamine ameliorates retinal photic injury in albino rats," *Cur. Eye Res.*, vol. 10, No. 2:133-144, 1991.
Sabel, et al., "A behavioral model of excitotoxicity: retinal degeneration, loss of vision, and subsequent recovery after intraocular . . . ," *Exp. Brain Res.*, vol. 106:93-105, 1995.

Siliprandi, et al., "N-methyl-d-aspartate-induced neurotoxicity in the adult rat retina," *Vis. Neurosci.*, vol. 8:567-573, 1992.
Gupta, et al., "Mannitol, dextromethorphan, and catalase minimize ischemic damage to retinal pigment . . . ," *Arch. Ophthal.* vol. 111:384-388, Mar. 1993.
Solberg, et al., MK-801 has neuroprotective and antiproliferative effects in retinal laser injury., *Invest. Ophthal. & Vis. Sci.*, vol. 38(7):1380-1389, Jun. 1997.
Carter, et al, "Ifenprodil and SL 82.0715 as cerebral anti-ischemic agents. III. Evidence for antagonistic . . . ," *Journal of Pharm. and Exp. Ther.* vol. 253(2):475-482, Aug. 1989.
Beart, et al., "Blockade by polyamine NMDA antagonists related to ifenprodil of NMDA-induced . . . ," *British Journal of Phar.*, vol. 114:1359-1364, 1995.
Chenard, et al., "Oxindole N-Methyl-D-aspartate (NMDA) antagonists," *Bioorganic & Medicinal Chemistry Letters*, vol. 3(1):91-94, 1993.
Chenard et al., "(1S,2S)-1-(4-Hydroxyphenyl)-2-(4-hydroxy-4-phenylpiperidino)-1-propanol:A potent new . . . ," *Journal of Medicinal Chemistry*, vol. 38:3138-3145, 1995.
Butler, et al., "(3R,4S)-3[4-(4-Fluorophenyl)-4-hydroxypiperidin-1-yl]chroman-4,7-diol:A conformationally . . . ," *Journal of Medicinal Chemistry*, vol. 41, 1172-1184, 1998.
Chenard, et al., Separation of a 1 adrenergic and N-methyl-d-aspartate antagonist activity in a series . . . , *Journal of Medicinal Chemistry*, vol. 34, 3085-3090, 1991.
Avenet, et al., "Antagonist properties of eliprodil and other NMDA receptor antagonists at rat NR1A/NR 2A . . . ," *Neuroscience Letters*, vol. 223:133-136, 1997.
Boeckman, et al., "Pharmocological properties of acquired excitotoxicity in Chinese hamster ovary cells . . . ," *Journal of Pharmacology and Exp. Therapeutic*, vol. 279(2):515-523, 1996.
Bath, et al., "The effects of ifenprodil and eliprodil on voltage-dependent $Ca^{2+}$ channels and in gerbil . . . ," *European Journal of Pharmacology*, vol. 299:103-112, 1996.
Biton, et al., "The NMDA receptor antagonist eliprodil (SL 82.0715) blocks voltage-operated . . . ," *European Journal of Pharmacology*, vol. 257:297-301, 1994.
Green, et al., "Pathologic findings of photic retinopathy in the human eye," *American Journal of Ophthalmology*, vol. 112:520-27, 1991.
Lambiase, et al., "Nerve growth factor delays retinal degeneration in C3H mice," *Graefes Arch. Clin. And Exp. Ophthal.*, vol. 234: S96-S100, 1996.
Scatton, et al., "Eliprodil Hydrochloride," *Drugs of the Future*, vol. 19(10):905-909, 1994.
Shahinfar, et al., "A pathologic study of photoreceptor cell death in retinal photic injury," *Current Eye Research*, vol. 10(1):47-59, 1991.
Abler, et al., "Photic injury triggers apoptosis of photoreceptor cells," *Investigative Ophthalmology & Visual Science*, vol. 35(Suppl):1517, 1994.
Chang, et al., "Apoptotic photoreceptor cell death after traumatic retinal detachment in humans," *Archives of Ophthalmology*, vol. 113:880-886, 1995.
Portera-Cailliau, et al., "Apoptotic photoreceptor cell deach in mouse models of retinitis pigmentosa," *Proceedings of National Academy of Science* (U.S.A.), vol. 91:974-978, 1994.
Buchi, Ernst R., Cell death in the rat retina after a pressure-induced ischaemia-reperfusion insult: an . . . , *Experimental Eye Research*, vol. 55:605-613, 1992.
Quigley, et al., "Retinal ganglion cell death in experimental glaucoma and after axotomy occurs by apoptosis," *Investigative Ophthalmology & Visual Science*, vol. 36(5):774-786, 1995.
Zigman, et al., "The response of mouse ocular tissues to continuous near-UV light exposure," *Investigative Ophthalmology & Visual Science*, vol. 14:710-713, 1975.
Noell, et al., "Retinal damage by light in rats," *Invest. Ophthal. & Vis. Sci.*, vol. 5(5):450-472, Oct. 1966.
Kuwabara, et al., "Retinal damage by visible light: An electron microscopic study," *Archives of Ophthalmology*, vol. 79:69-78, 1968.
LaVail, M.M., "Survival of some photoreceptor cells in albino rats following long-term exposure to continuous light," *Investigative Ophthalmology*, vol. 15(1):64-70, 1976.

Lawwill, T., "Effects of prolonged exposure of rabbit retina to low-intensity light," *Investigative Ophthalmology*, vol. 12(1):45-51, 1973.

Collier, et al., "Comparison of retinal photochemical lesions after exposure to Near-UV or short- . . . ," *Inherited and Environmentally induced Retinal Degenerations*, pp. 569-575, 1989.

Collier, et al., "Temporal sequence of changes to the gray squirrel retina after near-UV exposure," *Investigative Ophthalmology & Visual Science*, vol. 30(4):631-637, 1989.

Tso, M., "Photic maculopathy in rhesus monkey. A light and electron microscopic study," *Investigative Ophthalmology*, vol. 12:17-34, 1973.

Ham, et al., "The nature of retinal radiation damage: dependence on wavelength, power level and . . . ," *Vision Research*, vol. 20:1105-111, 1980.

Sperling, et al., "Differential spectral photic damage to primate cones," *Vision Research*, vol. 20:1117-1125, 1980.

Sykes, et al., "Damage to the monkey retina by broad spectrum fluorescent light," *Investigative Ophthalmology & Visual Science*, vol. 20:425-434, 1981.

Lawwill, T., "Three major pathologic processes caused by light in the primate retina: A search for mechanisms," *Transactions of the American Ophthalmology Society*, vol. 80:517-579, 1982.

Ehren, M., et al., *Inhibition of RPE proliferation, attachment and migration by carboxyamido-triazole (CAI), a drug which acts b modifying calcium mediated signal transduction*, Investigative Ophthalmology and Visual Science, vol. 38, No. 4 part 1-2 May 1997, p. S754.

Hahn, J.M., et al., *Calcium channel blocker mediated inhibition of retinal pigment epithelial cell contraction of a collagen gels*, Investigative Ophthalmology and Visual Science, vol. 37, No. 3, 1996, p. S393.

Hoffmann, S., et al., *Effect of the Calcium-antagonist verapamil on the serum induced proliferation of RPE cells in vitro*, Investigative Ophthalmology and Visual Science, vol. 37, No. 3, 1996, pp. S389.

Richter D., et al. *Growth inhibition of intraocular proliferative explants under in vitro conditions by verapamil*, Klinische Monatsblatter Fur Augenheilkunde, Sep. 1993, vol. 203, No. 3, pp. 206-211.

CALCIUM BLOCKERS TO TREAT PROLIFERATIVE VITREORETINOPATHY

This patent application is a continuation of U.S. patent application Ser. No. 10/436,902, filed on May 12, 2003 now U.S. Pat. No. 7,230,032, which is a continuation of U.S. patent application Ser. No. 10/038,215, now U.S. Pat. No. 6,573,280, filed Jan. 2, 2002, which is a continuation of U.S. patent application Ser. No. 09/445,832, now U.S. Pat. No. 6,380,261, which was filed on Dec. 13, 1999 as the U.S. National Patent Application of PCT/US98/12414, which was filed on Jun. 15, 1998 and was based on U.S. Provisional Application 60/051,962, which was filed on Jun. 30, 1997 in the name of Dreyer.

BACKGROUND OF THE INVENTION

This application relates to preventing, controlling reducing and/or treating proliferative vitreoretinopathy. Proliferative vitreoretinopathy (including epiretinal membrane formation) is a potentially devastating ophthalmic condition that can lead to blindness. It can develop after any penetration of the eye—surgical or traumatic. Predisposing conditions therefore include, but are not limited to, penetrating trauma, retinal tears, traction detachments, vitrectomy, and intraocular surgery. Any ophthalmic condition that precipitates or permits migration of retinal pigment is epithelium or glial cells can lead to the development of proliferative vitreoretinopathy. See Machamer (1978) British J. Ophthal. 62:737; Hilton et al. (1983) Ophthalmology 90:121.

SUMMARY OF THE INVENTION

I have discovered that glutamate causes migration and proliferation of retinal pigment epithelium and/or glial cells. The invention features the use of glutamate antagonists to reduce or control retinal pigment epithelium and/or glial migration and the subsequent development of proliferative vitreoretinopathy. Avoidance or management of proliferative vitreoretinopathy can be achieved by administering to the patient a compound capable of reducing glutamate-induced retinal pigment epithelium and/or glial migration in a concentration effective to reduce such migration.

While I do not wish to be bound to any specific theory, I conclude that one or more of the several types of calcium-permeable CNS ion channels mentioned below can be involved in controlling such migration, including: a) the various aspects of the NMDA (N-methyl-D-aspartate) receptor channel complex; b) the voltage-dependent $Ca^{2+}$ channels; and c) other channels directly coupled to glutamate (or excitatory amino acid) receptors. Such channels are reviewed in: Sommer, B. and Seeburg, P. H. "Glutamate receptor channels: novel properties and new clones" *Trends. Pharmacological Sciences* 13:291-296 (1992); Nakanishi, S., "Molecular Diversity of glutamate receptors and implications for brain function", *Science* 248:597-603 (1992).

One aspect of the invention generally features a method of treating, preventing, or reducing proliferative vitreoretinopathy in a patient by administering to the patient's retina an effective amount of a compound that reduces CNS neuronal damage incident to (associated with) calcium ion influx.

A second aspect of the invention features treating, preventing, or reducing proliferative vitreoretinopathy in a patient by administering to the patient's retina an effective amount of at least one of the compounds listed in one or more of Tables 2-5. below.

A third aspect of the invention features treating preventing or reducing proliferative vitreoretinopathy in a patient by administering to the patient's retina an effective amount of a compound that reduces glutamate related retinal cell migration, proliferation, or both.

The compound may be one of the so-called NMDA antagonists—i.e., it reduces neuronal damage mediated by the NMDA receptor complex. Alternatively, the compound antagonizes neuronal damage mediated by the voltage-dependent calcium channel. Other useful compounds are those which limit release of glutamate from cells or reduce the intracellular neurotoxic consequences of glutamate interaction with cell membrane glutamate receptors. Preferably, the compound crosses the blood-retinal barrier.

The patient may be anyone who has experienced, or is at risk for experiencing, penetrating trauma, retinal tear, traction detachment, vitrectomy, or intraocular surgery. The compound may be administered to the patient s topically, orally, or intravitreally, as well as by other routes described below. It may be administered chronically, i.e., over an extended period of a month or even six months or years.

The invention preferably will be used to treat lo patients having proliferative vitreoretinopathy or to treat patients prophylactically to avoid that condition. Preferably, the agent is administered over an extended period (e.g., at least six months and preferably at least one year). Those at risk for developing proliferative vitreoretinopathy include patients who have experienced penetrating trauma, retinal tears, traction detachments, vitrectomy, or intraocular surgery.

Particularly preferred compounds are antagonists of the NMDA receptor-channel complex. The term "NMDA receptor antagonists" includes several sub-types of NMDA antagonists including: a) channel blockers—i.e., antagonists that operate uncompetitively to block the NMDA receptor channel; b) receptor antagonists antagonists that compete with NMDA to act at the NMDA binding site; c) agents acting at either the glycine co-agonist site or any of several modulation sites such as the zinc site, the magnesium site, the redox modulatory site, or the polyamine site; d) agents which inhibit the downstream effects of NMDA receptor stimulation, such as agents that inhibit activation of protein kinase C activation by NMDA stimulation, antioxidants, and agents that decrease phosphatidylinositol metabolism.

Other compounds that are useful in the invention include voltage-dependent calcium channel antagonists, e.g. those which exert a substantial direct effect on glutamate toxicity mediated by the L-type voltage dependent $Ca^{++}$ channel in that they produce a statistically significant result in experiments measuring glutamate induced effects by the general method described in Karschian and Lipton, *J. Physiol.* 418: 379-396 (1989) or by other techniques for measuring antagonism of the L-type $Ca^{++}$ channel known to those in the art. (We contrast the direct effect so measured with the secondary effects of excitotoxicity mediated by other channels, which in turn causes flow through the voltage dependent $Ca^{++}$ channels.) Particular candidate compounds include Class I voltage dependent $Ca^{++}$ channel antagonists, e.g., phenylalkylamines.

Preferably, the compounds used cross the blood-retina barrier and can be administered chronically. Other useful agents act as antagonists of non-NMDA receptors (glutamate receptor types other than the NMDA receptor complex discussed above), and include agents which block inotropic glutamate receptors or interact with metabotropic glutamate receptors (nakanishi, supra). Still other agents act to limit (reduce) release of glutamate from cells, thereby acting upstream from the glutamate receptors in the excitatory neurotoxicity process. Still other agents may act by blocking downstream effects of glutamate receptor stimulation, e.g., the intracellular consequences of glutamate interaction with a cell membrane glutamate receptor, such as agents (like dantrolene) that block the rise in intracellular calcium following stimulation of membrane glutamate receptors.

The most preferred compounds are those capable of crossing the blood-retinal barrier; these compounds may be administered orally, intravenously, or topically and cross intervening barriers including the blood-retina barrier to reach the retinal ganglion cells. Compounds that do not freely cross the blood-retina barrier are less preferred; these compounds may be administered intravitreally to the retina. In the case of compounds that have an intermediate ability to cross the blood-retina barrier, the mode of administration will depend on the dosage required and other factors.

Among the preferred compounds are amantadine derivatives (e.g., memantine, amantadine, and rimantadine), nitroglycerin, dextorphan, dextromethorphan, and CGS-19755. See generally, the compounds listed in Table 2.

The invention is useful for the reduction or prevention (including prophylactic treatment) of damage as a result of proliferative vitreoretinopathy.

Other features and advantages of the invention will be apparent from the following description of the preferred embodiments thereof, and from the claims.

DESCRIPTION OF THE PREFERRED EMBODIMENTS SELECTION OF ANTAGONISTS

In view of our discovery that glutamate is associated with proliferative vitreoretinopathy, the invention features antagonists having certain specific characteristics: the ability to cross the blood-retina barrier; and the ability to be administered chronically. Within those guidelines, any suitable antagonist of the glutamate induced excitotoxicity may be used in accordance with the invention. As mentioned, in preferred embodiments, N-methyl-D-aspartate (NMDA) sub-type of glutamate receptor-channel complex may be used to reduce or prevent proliferative vitreoretinopathy-related injury. Many antagonists of the NMDA receptor have been identified (Watkins et al., Trends in Pharmacological Sci. 11:25, 1990, hereby incorporated by reference). There are several recognized sub-types of NMDA receptor including: a) channel blockers—i.e., antagonists that operate non-competitively to block the NMDA receptor channel; b) receptor antagonists—antagonists that compete with NMDA, acting at the NMDA binding site; c) agents acting at either the glycine co-agonist site or any of several modulation sites such as the zinc site, the magnesium site, the redox modulatory site, or the polyamine site; d) agents which inhibit the downstream effects of NMDA receptor stimulation such as agents that inhibit activation of protein kinase C activation by NMDA stimulation, antioxidants, and agents that decrease phosphatidylinositol metabolism.

Other compounds that are useful in this invention include non-NMDA receptor antagonists, such as agents which block other types of inotropic glutamate receptors or interact with metabotropic glutamate receptors; voltage-dependent calcium channel antagonists (against L, N, T, and P type channels) (Bean, B. P. Annu. Rev. Physiol. 51:367-384 (1989); Hess, P. Annu. Rev. Neurosci. 13:337-356 (1990)), and are described in greater detail below; and agents which act to decrease the release of glutamate, thereby acting upstream in the excitatory neurotoxicity process.

Table 1, below, lists various suitable NMDA and non-NMDA receptors which do not operate via the voltage-dependent $Ca^{++}$ ion channel. Tables 2-4 list antagonists of the voltage dependent $Ca^{++}$ channel, which can be used by themselves in connection with the first aspect of the invention, and which can also be used in combination with other antagonists in the second aspect of the invention.

TABLE 1

| NMDA Antagonist | NMDA Antagonists | NMDA Antagonists |
|---|---|---|
| 1. Competitive NMDA Antagonists (act at agonist binding site) | 2. Channel Blockers (Un-Competitive NMDA Antagonists) | 3. Antagonists at Glycine Site of the NMDA Receptor |
| CGS-19755 (CIBA-GEIGY) and other piperdine derivatives, D-2-amino-5-phosphovalerate, D-2-amino-7-phosphonoheptanoate (AP7) | MK-801 (Dizocilpine) and other derivatives of dibenzyocycloheptene (Merck) | Kyourenate, 7-chloro-kyourenate 5,7-chloro-kyourenate, thio-dervatives, and other derivatives (Merck) |
| CPP {[3-(2-carboxy-piperazin-4-y-propyl-1-phosphonic acid]} | Sigma receptor ligands, e.g. Dextrorphan dextromethorphan and morphinan derivatives (Hoffman La Roche) such as caramiphen and timeazole (which also block calcium channels) | Indole-2-caboxylic acid |
| LY 274614, CGP39551, CGP37849, LY233053, LY233536 | Ketamine, Tiletamine and other cyclohexanes | DNQX |
| O-phosphobornoserine | Phencyclidine (PCP) and derivatives, and pyrazine compounds | Quinoxaline or oxidiazole derivatives including CNQX, NMQX |
| MDL100, 453 | Memantine, amantadine, rimantadine and derivatives CNS 1102 (and related bi- and tri-substituted guanidines) | Glycine partial agonist (e.g. Hoecht-Roussel P-9939) |

TABLE 1-continued

| | Diamines<br>Canontokan peptide from<br>Cocus geographus<br>Agatoxin-489 | |
|---|---|---|
| 4. Polyamine Site of NMDA Receptor | 5. Redox Site of NMDA Receptor | 6. Other Non-Competitive NMDA Antagonists |
| Arcaine and related biguanidines and biogenic polyamines | Oxidized and reduced glutathione | Hoechst 831917189 |
| Ifenprodil and related drugs | PQQ (pyrroloquinoline quinone) | SKB Carvedilol |
| Diethylene-triamine SL 82.0715 | Compounds that generate Nitric Oxide (NO) or other oxidation states of nitrogen monoxide (NO+, NO−) including those listed in the box below | |
| 1,10-diaminodecane (and related inverse agonist) | Nitroglycerin and derivative, Sodium Nitroprusside, and other NO generating listed on p.5 of this table<br>Nitric oxide synthase (NOS) Inhibitors:<br>Arginine analogs including N-mono-methyl-L-argine (NMA): N-amino-L-arginine (NAA); N-nitro-L-arginine (NNA); N-nitro-L-arginine methyl ester; N-imino-ethyl-L-ornithine<br>Flavin Inhibitors: diphenyl-iodinium;<br>Calmodulin inhibitors, trifluoperizine<br>Calcineurin Inhibitors, e.g., FK-506 (inhibits calcineurin and thus NOS diphosphorylase) | |

| Table 1, Page 3 Inhibitors of Downstream Effects of NMDA | Inhibitors of Downstream Effects of NMDA | Non-NMDA Receptor Antagonist |
|---|---|---|
| 7. Agents to inhibit protein kinase C activation by NMDA stimulation (involved in NMDA toxicity) | 8. Downstream effects from Receptor Activation | 9A. Non-NMDA antagonists (Competitive) |
| MDL 27.266 (Merrill Dow) and triazole-one derivatives | 8a. To decrease phospshati-dylinositol metabolism | CNQX, NBQX, YM900, DNQX, PD 140532 |
| Monosialogangliosides (eg GM1 of Fidia Corp.) And other ganglioside derivatives LIGA20, LIGA4 (may also effect calcium extrusion via caldium ATPase) | kappa opioid receptor agonist: U50-488 (Upjohn) and dynorphan | AMOA (2-amino-3[3-9carboxy-methoxyl-5-methoxylisoxazol-4-yl]propionate) |
| | kappa opioid receptor agonist: PD117302, CI-977 | 2-phosphophono-ethyl phenylalamine derivatives, i.e. 5-ethyl, 5-methyl, 5-trifluoromethyl |
| | 8b. To decrease hydrogen peroxide and free radical injury, e.g. antioxidants | |
| | 21-aminosteroid (lazaroids) such as U74500A, U75412E and U74006F | 9B. Non-NMDA Non competitive antagonist |
| | U74389F, FLE26749, Trolex (water soluble alpha tocophenol), 3,5-dialkoxy-4-hydroxy-benzylamines | GYK152466 |
| | Compounds that generate Nitric Oxide (NO) or other oxidation states of | Evans Blue |

TABLE 1-continued

| | | |
|---|---|---|
| | nitrogen monoxide (NO+, NO−) including those listed in the box below Nitroglycerin and derivatives, Sodium Nitroprusside, and other NO generating listed on p. 5 of this table Nitric oxide synthase (NOS) Inhibitors: Arginine analogs including N-mono-methyl-L-arginine (NMA); N-amino-L-arginine (NAA); N-nitro-L-arginine (NNA); N-nitro-L-arginine methyl ester, N-iminoethyl-L-ornithine | |
| Agents Active at Metabotropic Glutamate Receptors | Decrease glutamate release | Drugs to decrease intracellular calcium following glutamate receptor stimulation |
| 10a Blockers of Metabotropic Glutamate Receptors AP3 (2-amino-3-phosphonprionic acid)<br><br>10b. Agonists of Metabotropic Glutamate Receptors (1S, 3R)-1-Amino-cyclopentane-1,3-dicarboxylic acid[(1S, 3R)-ACPD], commonly ref as 'trans'-ACPD | 11. Agents to decrease glutamate release<br><br>Adenosine, and derivatives, e.g. cyclohexyladenosine CNS1145<br><br><br>Conopeptides: SNX-111, SNX-183, SNX-230<br><br><br><br>Omega-Age-IVA, toxin from venom of funnel web spider Compounds that generate Nitric Oxide (NO or other oxidation states of nitrogen monoxide (NO+, NO−) including those listed in the box below Nitroglycerin and derivatives, Sodium Nitroprusside, and other NO generating listed on p. 5 of this table Nitric oxide synthase (NOS) Inhibitors: Arginine analogs including N-mono-methyl-L-arginine (NMA); N-amino-L-arginine (NAA) N-nitro-L-arginine (NNA); N-nitro-L-arginine methyl ester; N-iminoethyl-L-ornithine Additional NO− Generating compounds Isosorbide dinitrate (isordil) S-nitrosocaptopril (SnoCap) Serum albumin coupled to nitric oxide (SA-NO) Cathepsin coupled to nitric oxide (cathepsin-NO) Tissue plasminogen activator coupled to NO (TPA-NO) SIN-1 (also known as | 12a. Agents to decrease intracellular calcium release Dantrolene (sodium dantrium); Ryanodine (or ryanodine + caffeine) 12b. Agents Inhibiting intracellular Calcium ATPase Thapsigargin, cyclopiazonic acid, BHQ ([2,5-di-(tert butyl)-1,4-benzohydroquinone; 2,5-di(tert butyl)-1,4 benzohydroquinone]) |

TABLE 1-continued

SIN1 or molsidomine)
Ion-nitrosyl complexes
(e.g., nitrosyl-iron
complexes, with iron
in the Fe2+ state)
Nicorandil

TABLE 2

Antagonists of the Voltage Dependent Calcium Channels (N, L, T, P and other types)

dihydropyridines (e.g., nimodipine)
phenylalkylamines (e.g., verapamil, (S)-emopamil, D-600, D-888)
benzothiazepines (e.g., diltiazem and others)
bepridil and related drugs
diphenylbutylpiperdines
diphenylpiperazines (e.g., flunarizine/cinnarizine series)
HOE 166 and related drugs
fluspirilene and related drugs
toxins and natural compounds (e.g., snail toxins - ωconotoxin GVIA and GVIIA, maitotoxin, taicatoxin, tetrandine, hololena toxin, plectreurys toxin, funnel-web spider venom and its toxin fraction, agatoxins including ω-agatoxin IIIA and ω-agatoxin IVA.

TABLE 3

DIHYDROPYRIDINE CALCIUM CHANNEL ANTAGONISTS

| | |
|---|---|
| nifedipine | KW3049 |
| niludipine | oxodipine |
| PY108-068 (darodipine) | CD349 |
| mesudipine | TC81 |
| GX 1048 | YM-09730-5 or (4S)DHP |
| floridine | MDL72567 |
| nitrendipine | Ro18-3981 |
| nisoldipine | DHP-218 |
| nimodipine | nilvadipine |
| nicardipine | amlodipine |
| felodipine | 8363-S |
| PN200-110 (Isradipine) | iodipine |
| CV4093 | azidopine |

TABLE 4

OTHER CALCIUM CHANNEL ANTAGONISTS

| | |
|---|---|
| diclofurime | D-600 |
| pimozide | D-888 |
| prenylamine | Smith Kline 9512 |
| fendiline | ranolzine |
| perhexiline | lidoflazine |
| mioflazine | CERM-11956 |
| flunarizine/cinnarizine series | R-58735 |
| | R-56865 |
| verapamil | amiloride |
| dilfiazine | phenytoin |
| dipropervine | thioridazine |
| (S)-emopamil | tricyclic antidepressants |

In Vitro Assay

An antagonist may be tested for utility in the method of the invention by monitoring its effect on proliferative retinopathy as follows.

Cultured fibroblasts will be injected into the vitreous of the rabbit eye. After two weeks, the degree of vitreopathy can be assessed histologically. At the time of the initial insult, the animals will be treated with the compound under consideration.

Such models are well known. A few examples (hereby incorporated by reference) included Kiumura et al. *Human Gene Therapy*, 1:799-808 (1996); Sakamoto. et al., *Ophthalmology* 10:1417-1421 (1995); Handa et al. *Experimental Eye Research* 62:689-696 (1996); Berger et al. 37: 2318-1325 (1996); de Souza et al. *Ophthalmologica* 209: 212-216 (1995); Nakagawa et al. *Ophthalmology & Visual Science* 36:2388-2395 (1995); Steinhorat et al. *Archive for Clinical & Experimental Ophthalmology* 232:347-354 (1994).

Use

An effective receptor antagonist will cause a decrease in proliferative vitreoretinopathy. As described above, the preferred compounds which cross the blood-retinal barriers are preferably administered topically or orally in known, physiologically acceptable vehicles including tablets, liquid excipients and suspensions. Those skilled in the art will appreciate how to formulate acceptable therapeutics.

Antagonists may be compounded into a pharmaceutical preparation, using pharmaceutical compounds well-known in the art; the exact formulation and dosage of the antagonist compound depends upon the route of administration. Generally, the effective daily dose of the antagonists will range from 0.01 to 1000 mg/kg.

Other Embodiments

Other embodiments are within the following claims. In the method of the invention, a useful compound may be administered by any means that allows the compound access to the retina. The compounds useful in the method include antagonists of excitatory amino acid receptors (both NMDA and non-NMDA subtypes) that act to reduce retinal cell migration or proliferation or reduce binding of glutamate to the NMDA receptor. The antagonists can act at a modulatory site or a co-agonist site or by blocking the chain of events initiated by receptor activation.

Other embodiments are within the following claims.

What is claimed is:

1. A method for treating an ophthalmic condition involving the retinal pigment epithelium of an eye of an individual, comprising:
   administering an amount of an excitatory amino acid receptor antagonist to the individual, the amount being effective in reducing glutamate-induced effects on the retinal pigment epithelium of the eye of the individual.

2. The method of claim 1, wherein the excitatory amino acid receptor antagonist is an NMDA receptor antagonist.

3. The method of claim 2, wherein the NMDA receptor antagonist is an agent that acts at the polyamine site of an NMDA receptor.

4. The method of claim 3, wherein the agent is ifenprodil.

5. The method of claim 2, wherein the NMDA receptor antagonist is an uncompetitive NMDA receptor antagonist.

6. The method of claim 5, wherein the NMDA receptor antagonist is memantine.

7. The method of claim 1, wherein the excitatory amino acid receptor antagonist is administered to the patient by a route selected from the group consisting of an oral route, an intravenous route, and a topical route.

8. The method of claim 1, wherein the administration of the excitatory amino acid receptor antagonist is effective in treating or reducing proliferative vitreoretinopathy.

9. The method of claim 1, wherein the administration of the excitatory amino acid receptor antagonist is effective in preventing proliferative vitreoretinopathy resulting from penetrating trauma, retinal tear, traction detachment, vitrectomy or intraocular surgery.

10. The method of claim 1, wherein the amount of the excitatory amino acid receptor antagonist is effective in reducing at least one of glutamate-induced retinal pigment epithelium migration, retinal pigment epithelium proliferation, glial migration, and glial proliferation.

11. A method of treating a retinal pigment epithelium condition of an eye of an individual, comprising:
   administering a therapeutically effective amount of a glutamate receptor antagonist to the individual.

12. The method of claim 11, wherein the glutamate receptor antagonist is an NMDA receptor antagonist.

13. The method of claim 12, wherein the NMDA receptor antagonist is an agent that acts on a polyamine site of an NMDA receptor.

14. The method of claim 12, wherein the NMDA receptor antagonist is an amantadine derivative.

15. The method of claim 14, wherein the amantadine derivative is memantine.

16. The method of claim 11, wherein the administration is effective to treat at least one of retinal pigment epithelium migration and retinal pigment epithelium proliferation.

17. The method of claim 11, wherein the administration is effective in treating proliferative vitreoretinopathy.

18. The method of claim 11, wherein the excitatory amino acid receptor antagonist is administered to the patient by a route selected from the group consisting of an oral route, an intravenous route, and a topical route.

* * * * *